Figure 1:
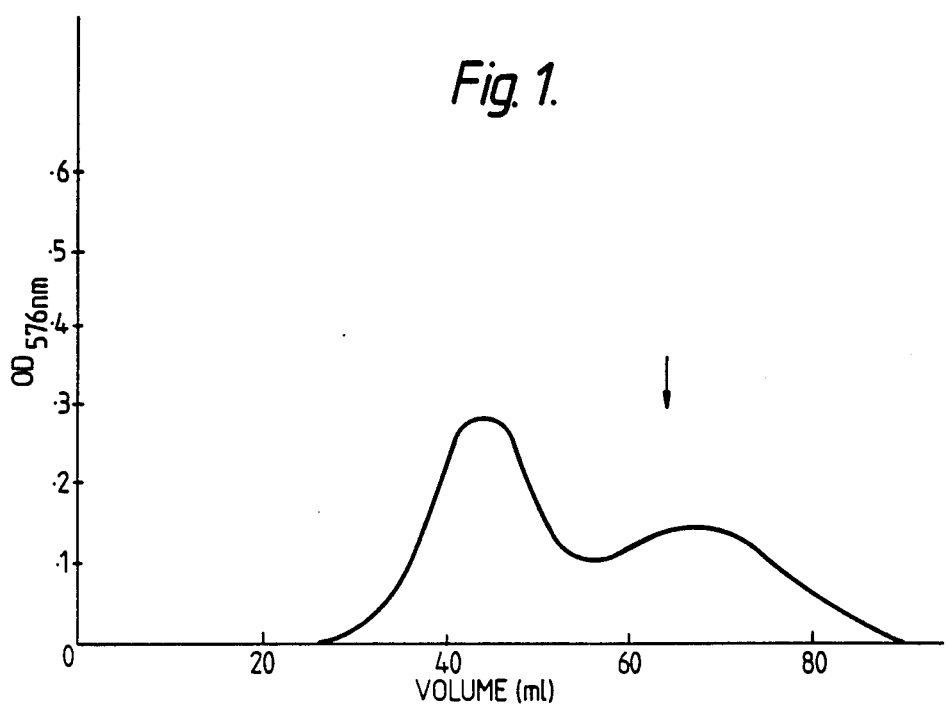

United States Patent [19]

Wong

[11] Patent Number: 4,710,488

[45] Date of Patent: Dec. 1, 1987

[54] HEMOGLOBIN INOSITOL PHOSPHATE COMPOUNDS

[75] Inventor: Jeffrey T. Wong, Don Mills, Canada

[73] Assignee: Fisons plc, Ipswich, England

[21] Appl. No.: 906,371

[22] Filed: Sep. 12, 1986

Related U.S. Application Data

[62] Division of Ser. No. 662,588, Oct. 19, 1984, Pat. No. 4,650,786.

[30] Foreign Application Priority Data

Oct. 28, 1983 [GB] United Kingdom ............... 8328917

[51] Int. Cl.$^4$ ..................... A61K 35/14; C07K 13/00
[52] U.S. Cl. ........................................ 514/6; 424/101; 530/385
[58] Field of Search ................... 530/385; 514/6; 424/101

[56] References Cited

U.S. PATENT DOCUMENTS

| | | | |
|---|---|---|---|
| 4,053,590 | 10/1977 | Bonsen et al. | 530/385 |
| 4,064,118 | 12/1977 | Wong | 530/385 |
| 4,136,093 | 1/1979 | Bonhard et al. | 530/385 |
| 4,336,248 | 6/1982 | Bonhard et al. | 530/385 X |
| 4,343,715 | 10/1982 | Bonaventura et al. | 514/6 X |
| 4,401,652 | 8/1983 | Simmonds et al. | 530/385 X |
| 4,412,989 | 11/1983 | Iwashita et al. | 530/410 X |
| 4,473,496 | 9/1984 | Scannon | 530/385 |
| 4,473,563 | 9/1984 | Nicolau et al. | 424/101 X |
| 4,600,531 | 7/1986 | Walder | 530/385 |

Primary Examiner—Howard E. Schain
Attorney, Agent, or Firm—Marshall, O'Toole, Gerstein, Murray & Bicknell

[57] ABSTRACT

There is described a water soluble compound having a molecular weight of from about 70,000 to about 2,000,000, and having the formula I, $$(PS)-X-(HB)-Z \qquad \text{I}$$

where
PS represents a physiologically acceptable polysaccharide of molecular weight from about 2,000 to about 2,000,000,
X represents a covalently bonded chemical bridging group,
HB represents a haemoglobin residue, and
Z represents an oxygen affinity reduced ligand, containing 2 or more phosphate groups.

There is also described haemoglobin linked to an oxygen affinity reducing ligand derived from inositol phosphate, and polymers of such linked haemoglobin.

Processes for making the compounds, and their formulation and use as oxygen transporting agents, are also described.

5 Claims, 4 Drawing Figures

HEMOGLOBIN INOSITOL PHOSPHATE COMPOUNDS

This is a division of application Ser. No. 662,588 filed Oct. 19, 1984, now U.S. Pat. No. 4,650,786.

This invention relates to blood substitutes and methods for their preparation.

U.S. Pat. No. 4,064,118 describes a composition useful as a blood substitute or blood extender composition which comprises the water soluble product of covalently coupling haemoglobin with dextran or hydroxyethyl starch having a molecular weight of from about 5,000 to about 2,000,000. This U.S. patent also describes a process for preparing such a composition, which comprises chemically coupling haemoglobin with dextran or hydroxyethyl starch of a molecular weight from about 5,000 to about 2,000,000.

It has however been found that, as compared with haemoglobin, the products according to U.S. Pat. No. 4,064,118 tend to show a somewhat greater affinity for oxygen, but retain the essential oxygen transporting and releasing capability of haemoglobin. As measured by the half-saturation oxygen tension, the dextran-haemoglobin complex prepared by method I of U.S. Pat. No. 4,064,118 shows approximately 2.5-fold greater affinity for oxygen than does free haemoglobin.

Pyridoxal-5-phosphate is known to bind to haemoglobin in a reversible manner, and it is also known that this binding can be made irreversible by reduction, both the reversibly and the irreversibly bound products having less strong oxygen binding characteristics than the haemoglobin itself. However, it has been found that covalent derivatization with pyridoxal-5'-phosphate fails to reduce the oxygen affinity of dextran-haemoglobin to approach that of haemoglobin derivatized with pyridoxal-5'-phosphate (PLP-Hb). An oxygen affinity close to or below that of PLP-Hb is considered desirable for a satisfactory haemoglobin-based blood substitute.

We have now found that physiologically acceptable polysaccharide haemoglobin complexes, for example as described in U.S. Pat. No. 4,064,118, can be made in modified form having a lower oxygen affinity than hitherto.

According to the invention we provide a water soluble compound having a molecular weight of from about 70,000 to about 2,000,000, and having the formula I, (PS)—X—(HB)—Z    I where
PS represents a physiologically acceptable polysaccharide of molecular weight from about 2,000 to about 2,000,000,
X represents a covalently bonded chemical bridging group,
HB represents a haemoglobin residue, and
Z represents an oxygen affinity reducing ligand, containing 2 or more phosphate groups.

We prefer Z to be a polyol, two or more of the hydroxy groups of which are esterified with phosphoric acid. We particularly prefer Z to contain from 2 to 6, and more preferably 2 to 4, phosphate groups. When Z is a phosphate ester of a polyol, at least 2, and preferably all, of the hydroxy groups have been esterified with phosphoric acid. We also prefer Z to contain from 4 to 8 carbon atoms and to be a straight chain group. We further prefer Z to comprise a polyol in which each of the carbon atoms (other than at least one of the terminal carbon atoms) carries an optionally phosphoric acid esterified hydroxy group.

The Z group may be linked to the haemoglobin in a wide variety of ways which will be readily recognised by those skilled in the art.

Thus according to the invention we also provide a process for the production of a compound of formula I, which comprises (a) linking a compound of formula II, (PS)—X—(HB)    II in which PS, X and HB are as defined above, with a compound capable of providing a Z ligand, (b) linking a compound of formula III, (HB)—Z    III in which HB and Z are as defined above, with a polysaccharide PS, or (c) producing a reduced form of a compound of formula I, by reduction of a corresponding compound of formula I containing a reducible double bond.

Thus for example the Z group may be linked to an amino group on the haemoglobin by means of an amide linkage, RCONH(HBx)—X—(PS)

in which X and PS are as defined above, (HBx)NH is a haemoglobin residue, and RCO is a Z group.

Such a linkage may be made by conventional acylation techniques, e.g. converting a compound RCOOH to an active ester therof, e.g. an N-hydroxysuccinimide ester, and reacting the resulting ester with the preformed polysaccharide - haemoglobin complex. However, such acylation reactions are somewhat unspecific and may lead to linkage of the Z group to less preferred positions on the haemoglobin.

We therefore prefer the Z group to be linked to the haemoglobin through a Schiff's base linkage, and preferably a reduced Schiff's base linkage, R—CH=N—(HBx)—X—(PS)

or,

R—CH$_2$—NH—(HBx)—X—(PS)

in which
X and PS are as defined above,
(HBx)—N= and (HBx)—NH— are haemoglobin residues, and
R—CH= or R—CH$_2$— is a Z group.

Such linkages may be made by conventional techniques, e.g. reacting an aldehyde RCHO with the preformed polysaccharide—haemoglobin complex, followed if necessary by selective reduction of the resulting Schiff's base. Suitable reducing agents include diethylamine borane or sodium cyano borohydride, or more preferably dimethylamine borane or sodium borohydride.

The linkage of the Z group to the (PS)—X—(HB) moiety is effected by procedures which are not affected by the size of the (PS)—X—(HB) moiety. Thus a wide range of sizes of product molecules can be made with differing ranges of polysaccharide to haemoglobin ratios.

We prefer the Z group to be derived from an inositol phosphate.

Inositol phosphates are known compounds and may be made and isolated in a manner which is also known per se. We particularly prefer the Z group to be derived from inositol tetraphosphate, e.g. from a mixture containing a major proportion of inositol tetraphosphate and a minor proportion of other inositol phosphates.

Thus the compound RCHO is preferably an inositol phosphate aldehyde, and more preferably an inositol phosphate dialdehyde of formula IV,

   IV in which at least 2, and preferably 4, of the groups Rx are phosphate groups and the remainder are —OH groups. Compounds of formula IV in which less than four groups Rx are phosphate groups exist as structural isomers and also as a variety of stereoisomers. Compounds of formula IV in which all four groups Rx are phosphate groups exist as a variety of stereoisomers. The compounds of formula IV may, if desired, be separated into their various structural and/or optical isomeric forms, using conventional techniques known per se. Alternatively, and preferably, the compounds of formula IV may be used as a mixture for further reaction with the haemoglobin or haemoglobin-polysaccharide complex.

The compounds of formula IV can be made by selective oxidation of an appropriate inositol phosphate having two adjacent free hydroxy groups. The oxidation may suitably be carried out using mildly oxidising conditions, e.g. by use of a perhalo acid, such as periodic acid.

The reaction may conveniently be carried out at a low pH or an elevated temperature, particularly when an inositol tetraphosphate is used as starting material.

The polysaccharide-haemoglobin complex may be derived from a wide variety of polysaccharides, e.g. a hydroxy alkyl starch (such as hydroxyethyl starch), inulin or preferably dextran. More particularly we prefer the complex to be one which has been prepared by the reaction of haemoglobin with N-bromoacetylaminoethylamino dextran as described by Tam, Blumenstein and Wong (1976) Proc. Nat. Acad. Sci. USA 73, 2128–2131 or Example 1 of British Patent Specification No. 1,549,246. We prefer the polysaccharide to be of molecular weight of from about 5,000 to 2,000,000, e.g. to be of average molecular weight 10,000 to 100,000. We prefer the polysaccharide to be a dextran of average molecular weight 70,000, 40,000 or 20,000.

A specific dextran-haemoglobin complex which may be used is a 1:1 complex between human haemoglobin and dextran of about 20,000 molecular weight (J. E. Chang and J. T. Wong, Canadian Journal of Biochemistry, Vol. 55, pp 398–403, 1977).

The proportion of Z groups in the polysaccharide complex (or in the compound of formula III) is preferably such that the phosphate to haemoglobin ratio is in the range 2 to 16:1, preferably 4 to 16:1 as determined by the method described in Example 1.

When a dialdehyde is used to produce the group Z some cross-linking between haemoglobin moieties may take place or the two aldehyde groups may react with different amino groups on the same haemoglobin molecule.

The modified haemoglobins of formula (HB)-Za in which Za is a group derived from an inositol phosphate, and in particular in which Z is derived, as described above, from an inositol phosphate aldehyde, are new compounds and form a feature of the present invention. These new modified haemoglobins have oxygen transporting capability and, in addition to their utility for linking to a polysaccharide, are useful in their own right, or in polymerised form, as oxygen transporters capability.

Thus according to the invention we further provide polymerised (HB)-Za and a process for the production of polymerised (HB)-Za, which comprises polymerisation of (HB)-Za.

The polymerisation of the (HB)-Za may be carried out using processes which are known per se for the polymerisation of haemoglobin, e.g. by reaction of the haemoglobin with glutaraldehyde, for example at a temperature of 0° to 10° C. in an aqueous solution. The reaction may be carried out in a buffer to maintain an approximately neutral pH. The (HB)-Za need not be deoxygenated before polymerisation. The polymerised product is advantageous in that its oxygen dissociation curve is right shifted compared to known polymerised haemoglobins or modified polymerised haemoglobins. The degree of polymerisation can vary with the particular purpose for which the product is desired. However, in general too high a degree of polymerisation will make the solutions of the polymer too viscous while too low a degree of polymerisation will leave many free haemoglobin molecules which may cause damage to the kidneys.

As an alternative to linking the Z group to the preformed haemoglobin polysaccharide complex (process a) above), the Z group may first be attached to the haemoglobin, e.g. using the techniques described above or other conventional linking techniques. The modified haemoglobin may then, if desired, be further linked to the polysaccharide (process b) above), e.g. using the techniques described in U.S. Pat. No 4,064,118.

The haemoglobin referred to in this specification may be derived from any appropriate animal, e.g. a bovine animal, but is preferably human haemoglobin.

The compounds of the invention, i.e. compounds of formula I, compounds Hb-Za and polymerised Hb-Za, are useful in that they have oxygen transporting capability. Thus the compounds are useful as immobilised oxygen extractants, for example in the system described in U.S. Pat. No. 4,343,715. The compounds are also indicated for use in blood substitute or blood expander compositions. Thus the compounds may be used to provide enhanced oxygenation of poorly perfused tissues. Such poorly perfused tissues may be present in cancerous growths, in cases of myocardial infarction or in cases of cerebral haemorrhage. The compounds may also be used as blood substitutes, e.g. for the victims of accidents or violence; where blood typing and matching is not possible or is not possible in the time available; where patients are at risk from, or refuse, normal blood transfusion; for the purpose of delivery of oxygen to tissues or organs which are to be preserved; for priming extracorporeal circulatory systems; or for other situations where erythrocytes are normally indicated.

The compounds may be administered to the patients concerned in admixture with a pharmaceutically acceptable exicipient, diluent or carrier, for example as an aqueous solution, which may be a buffered balanced salt solution. In general the compounds will be administered using types of formulations, packages and forms of administration which are conventional for the administration of blood plasma expanders. The compounds may also be freeze dried, optionally with a cryoprotective agent, and subsequently be reconstituted for use.

The amount of the compound which is administered will vary with the size, condition of the patient and treatment desired. However, in certain severe instances substantially all the patient's blood may be replaced by a formulation containing a compound of the invention.

The compounds of formula I, and the other compounds of the invention, are advantageous in that they possess more desirable oxygen absorption and release properties than similar known compounds. Thus certain compounds of the invention have oxygen dissociation curves (cf Example 3) which are more right shifted than phosphopyridoxylated haemoglobin. The compounds of the invention are also advantageous in that they may be prepared easily and in relatively high yield.

Molecular weights in this specification are expressed as Mw rather than Mn.

The invention is illustrated, but in no way limited by the following Examples.

EXAMPLE 1

(a) Preparation of Inositol Tetrakisphosphate

Sodium phytate (inositol hexaphosphate) was dephosphorylated at with soluble wheat phytase as described by R. V. Tomlinson and C. E. Ballou, Biochemistry 1, 166–171(1962). Alternatively wheat bran washed twice with 50% ethanol and once with 95% ethanol may be used as the source of phytase. Dephosphorylation was allowed to proceed until no significant amounts of inositol hexaphosphate or inositol pentaphosphate remained in solution. The amount of phytase employed was chosen so that this procedure required about 72 hours. The reaction mixture was clarified by filtration followed by centrifugation. IM $FeCl_3$ was added to the resulting solution to give a 3:1 molar ratio of $FeCl_3$: original phytate. The yellow precipitate was collected by centrifugation and resuspended in distilled water. Solid NaOH was added to the suspension to give pH 12, and the mixture was stirred and maintained at pH 12 for 3 hours. After filtration, the filtrate was neutralised with acetic acid to pH 5.2. The filtrate obtained from 5 liters of digest (containing originally 50 mM inositol hexaphosphate) was loaded on a 1 liter column of Dowex-1 resin equilibrated with distilled water. After loading, the column was washed with 1 liter distilled water, and eluted with 7 liters of 0.3 N HCl and then 4 liters of 1 N HCl. Fractions containing the inositol tetraphosphate were precipitated with 3 volumes of 95% ethanol. After standing overnight at 4° C., the supernatant was poured off, leaving a viscous precipitate. Absolute ethanol was added until the precipitate turned into a white powder. The powder was washed with absolute ethanol, 1:1 ethanol:ether and finally ether to yield the desired product.

(b) Oxidation of Inositol Tetrakisphosphate

A solution of 11g of inositol tetrakisphosphate (prepared as in step a)) in 322 ml of 0.6 M $HIO_4.2H_2O$, was incubated in the dark at 22° C. for eight hours. The reaction mixture was neutralised to pH 5.2 with 5N KOH, kept at 0° C. for 10 minutes and then centrifuged to remove $KIO_4$. Ascorbic acid (56.7 g) was added to the supernatant. After 10 minutes 3 volumes of ethanol were added and the mixture was kept at 4° C. for 1 hour. A clear viscous precipitate was collected by centrifugation. The precipitate was added to 100 ml of absolute ethanol. Upon trituration the precipitate became more solid, and eventually broke up into a powder as the ethanolic supernatant was replaced by 4 changes, 50 ml each, of absolute ethanol. The resulting white powder was washed with ethanol, 1:1 ethanol:ether and ether successively, and air dried. The yield was 7.7 g of the dialdehyde derivative of inositol tetrakisphosphate (FPA).

(c) Covalent Linkage of FPA to dextran haemoglobin with dimethylamine-borane (DMAB)

To 0.25 ml 6% w/w (measured on the haemoglobin alone) dextran haemoglobin (Dx-Hb) produced by the method of Example 1 of BP No. 1,549,246, save that dextran of molecular weight 20,000 was used, in 0.05M (bis-[2-hydroxyethyl] amino-tris-[hydroxymethyl])methane (bis-tris) pH 7.4, was added 1.25 mg of FPA in 0.17 ml 0.05 M sodium acetate buffer, pH 5.2 (about 7.3 FPA:1 Dx-Hb). The pH of the mixture was adjusted to 7.4 with dilute NaOH, 0.025 ml of 0.5 M dimethylamine borane (DMAB) was added, and the solution was incubated for 2 hours at 0° C. The resulting mixture was applied to a 30 ml Sephadex G25 column equilibrated in 0.1 M 2-amino-2-(hydroxymethyl)-1,3-propandiol (tris) 1N NaCl pH 8.5 buffer, and run at 4° C. The first two-thirds of the peak was collected, dialysed against bis-tris buffer, 0.05M, pH7.4 overnight and then used for oxygen dissociation determination. The use of the Sephadex column may, if desired, be omitted.

(d) Covalent Linkage of FPA to Dx-Hb with $NaBH_4$

To 0.25 ml 6% Dx-Hb (as used in c) above) in 0.05M bis-tris pH 7.4 was added 3.41 mg of FPA in a 20 mg/ml solution (20FPA:1Dx-Hb). The final pH of the solution was 7.0. After a 20 minute incubation at 0° C., 0.025 ml of 0.8M $NaBH_4$ was added. The solution was incubated for a further 2 hours at 0° C. The reaction mixture was then applied to a 30 ml Sephadex G25 column equilibrated in 0.1M tris 1N NaCl pH 8.5 and run at 4° C. The first two-thirds of the peak was collected, dialysed as in paragraph c) above, and used for oxygen dissociation determination. Again the use of the Sephadex column, may, if desired, be omitted.

In an alternative method 0.2 ml of 6% Dx-Hb (as used in c) above) in 0.05M bis-tris pH 7.4 was added 0.68 mg of FPA in a 5 mg/ml solution (5FPA:1Dx-Hb). The mixture was incubated at 0° C. for 20 minutes, and 0.02 ml of 0.5M $NaBH_4$ was added at 0° C., over a period of 2 hours with constant stirring.

(e) Covalent Linkage of FPA to Hb with Dimethylamine-Borane or $NaBH_4$

To 0.25 ml 6% w/w haemoglobin dissolved in 0.05M bis tris at pH 7.4, was added 1.25 mg of FPA in 0.17 ml 0.05M sodium acetate buffer, pH 5.2. The pH of the mixture was adjusted to 7.4 with dilute NaOH, 0.025 ml of 0.5M dimethylamine borane was added, and the solution was incubated for 2 hours at 0° C. The reaction mixture was applied to a 30 ml Sephadex G25 column equilibrated in 0.1 M tris buffer, pH 8.5, containing 1 N NaCl, and run at 4° C. The first two-thirds of the peak was collected, dialysed against bis-tris buffer, 0.05M, pH 7.4 overnight and then used for oxygen determination. (The use of the Sephadex column may, if desired, be omitted.) The FPA-Hb so obtained has an oxygen dissociation curve that is right-shifted as compared to free Hb, and therefore may be employed as oxygen carrier where a low affinity for oxygen is of importance, either for the purpose of blood substitution or for incorporation into an immobilised oxygen extractant. NaBH$_4$ may be used in place of the DMAB. The FPA-Hb so produced is also useful in parts (f) and (g) below.

(f) Covalent Linkage of Cyanogen Bromide-Activated Dextran to FPA-Hb 2 g of dextran with molecular weight of 70,000 was dissolved in a mixture of 80% formamide-20% water v/v, and the solution was chilled to −15° C. 1.6 g of CNBr in 3.2 ml of 80% formamide-20% water v/v at 4° C. was then added with stirring. Further addition of 15.1 ml of 1.5M triethylamine in dimethyl formamide at −15° C. was carried out dropwise with stirring. After incubation for 10 minutes at −15° C., one volume of acetone (at −20° C.) was added to the mixture to precipitate the activated dextran. The precipitate was washed twice with acetone (−20° C.) by centrifugation, once with ether, and air-dried to yield an activated dextran. 35 mg of the activated dextran was added to 1 ml of FPA-Hb (3% with respect to Hb jin 0.05 M bis-tris, pH 7.4, and the solution was held at 0° C. for 16 hours.

0.15 ml of the FPA-Dx-Hb obtained by this method (8% with respect to Hb) was separated from the uncoupled FPA-Hb by chromatography on a 118 ml Sephadex G150 column to produce the optical density trace at 576 nm shown in FIG. 1. The arrow indicates the position of uncoupled FPA-Hb.

(g) Preparation of Poly-FPA-Hb Using Glutaraldehyde as Polymerising Agent

Figure 2:
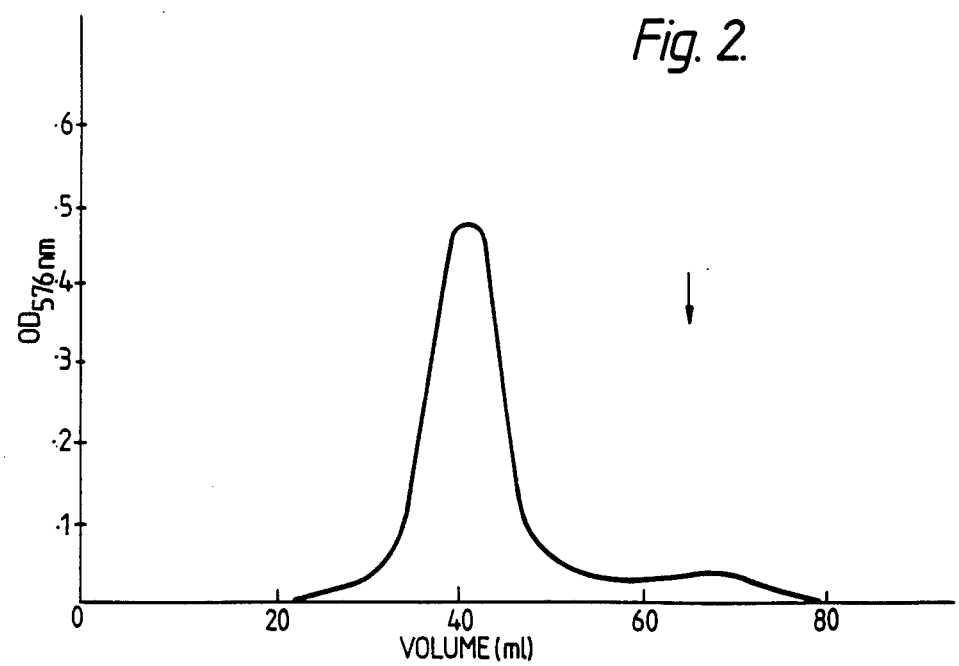

To 6.5 ml of FPA-Hb (6% with respect to Hb) in 0.1 M sodium phosphate buffer, pH 7.5, at 4° C., was added 0.195 ml of 5% glutaraldehyde in the same buffer. The mixture was kept at 4° C. for 16 hours and 0.15 ml of the mixture separated by chromatography on 118 ml of a Sephadex G150 column to produce the optical density trace at 576 nm shown in FIG. 2. The arrow indicates the position of free Hb.

Phosphate Determination

Up to 0.5 ml aliquots of the FPA-Dx-Hb or FPA-Hb solutions were digested by addition of 1.2 ml of 70% HClO$_4$, and then boiling until clear. 8 ml H$_2$O, 0.05 ml 5% ammonium molybdate and 0.05 ml 0.25% 1-amino-2-naphthol-4-sulphonic acid were then added. The resulting solutions were boiled for 10 minutes and the absorbance or optical density at 820 nm was read to determine phosphate concentration.

The haemoglobin concentration was determined by the method of D. L. Drabkin and J. H. Austin, J Biological Chemistry, Vol. 112, pp51-65 (1935).

| Preparation | Reduction Method | Phosphate/Hb$_4$ |
|---|---|---|
| FPA-Dx-Hb made from bromodextran MW 20,000 and human Hb | DMAB | 8.4:1 |
| FPA-Dx-Hb made from bromodextran MW 20,000 and human Hb | NaBH$_4$ | 4.8:1 |
| FPA-Dx-Hb made from bromodextran MW 20,000 and bovine Hb | DMAB | 10.9:1 |
| FPA-Hb made from human Hb | DMAB | 10.4:1 |

-continued

| Preparation | Reduction Method | Phosphate/Hb$_4$ |
|---|---|---|
| FPA-Hb made from bovine Hb | DMAB | 7.6:1 |

(Note:)
FPA-Dx-Hb obtained by linking dextran to FPA-Hb and polyFPA-Hb both start from FPA-Hb, therefore their phosphate/Hb$_4$ ratio will be identical to that of the parent FPA-Hb).

EXAMPLE 2

(a) 0.5 Mmole of 2,3-diphosphoglycerate was dissolved in 10 ml water and passed through pyridine-form of Dowex(or AG)-50 column. The effluent was collected and concentrated under reduced pressure. Water was removed by means of adding anhydrous pyridine and concentrating. Remaining water and pyridine were removed by washing with anhydrous dimethyl formamide (twice) until there was no smell of pyridine 6 Mmole of aminoacetaldehyde diethylacetal was added using anhydrous dimethyl sulphoxide as solvent, and mixed by shaking. 6 Mmole of dicyclohexylcarbodiimide was added and the mixture stirred for 3–4 hours at room temperature. A small amount of water was then added and the precipitate was filtered off. The filtrate was extracted (3×) with anhydrous ether in order to remove residual reactants and the solution concentrated to dryness to yield a white powder product.

(b) The crude product of step (a) (equivalent to about 0.5 Mmole of original 2,3-diphophroglycerate) was dissolved in a small quantity of water. The solution was passed through Dowex-50 H$^+$-form to remove free amine. The acidic portion of effluent was collected, concentrated to about 2 ml, and 0.5 ml 1 N HCl added. The resulting solution was left at 4° C. for 30–60 minutes and an equivalent amount of NH$_4$HCO$_3$ was added to adjust the pH to about 7.

(c) 3 μmoles of 6% dextran-haemoglobin (either oxygenated or deoxygenated), produced by the method of Example 1 of BP No. 1,549,246, was dissolved in 0.05M tris at pH 7.4. The product of step (b) (15 μmole) and sodium cyanoborohydride (60 μmole) were added and the reaction mixture maintained at room temperature for 2 hours. Excess product of step (b) was then removed either (i) by dialysis against 1M NaCl/0.05M tris at pH 8.5, or (ii) by passage through Sephadex C25 equilibrated with 1M NaCl/0.05M tris at pH 8.5, and collection of the front end peak.

EXAMPLE 3

The oxygen dissociation curves of the products of Example 1, and of the starting haemoglobin dextran were determined using the method of Benesch, MacDuff and Benesch (1965) Anal. Biochem 11 81–87 (1965), but using a temperature of 24° C. and bis-tris buffer, 0.05M, at a pH of 7.4.

Figure 3:
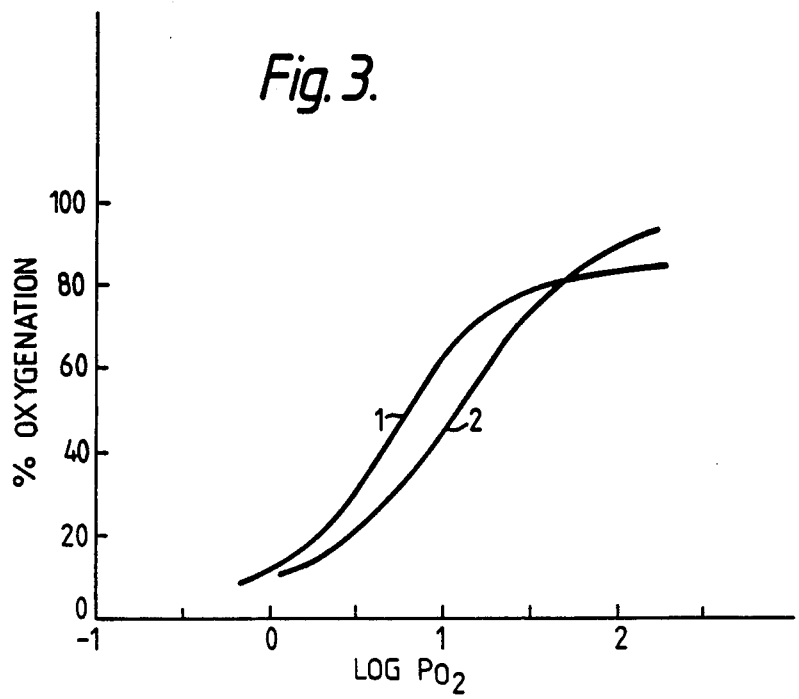
Figure 4:
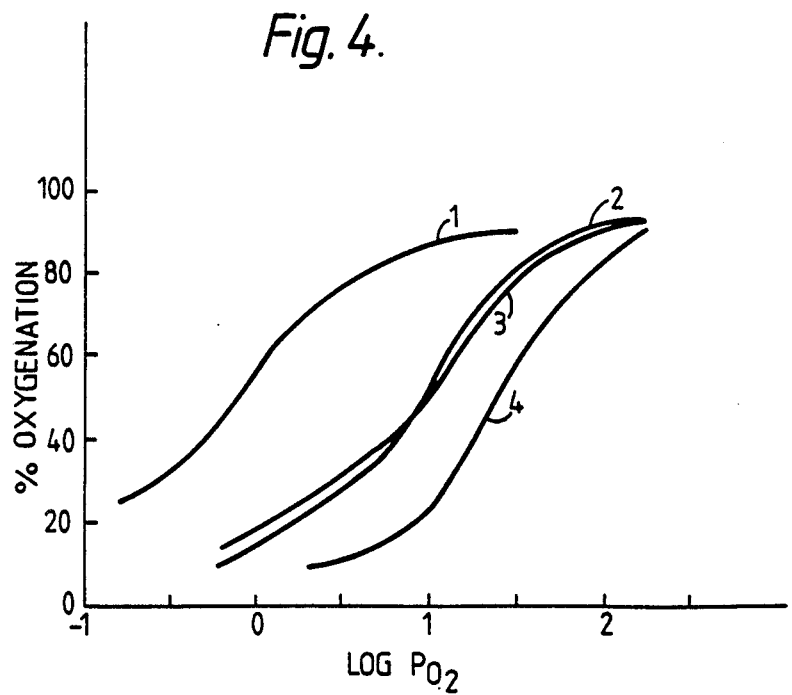

The results are shown in the attached FIGS. 3 and 4.
FIG. 3 shows the result for the product of Example 1g) before separation on the Sephadex column.
FIG. 4 shows at 1 the result for the dextran haemoglobin starting material for Example 1c), at 2 the result for the product of Example 1d), at 3 the result for the product of Example 1c) and at 4 the result for the product of Example (e) using DMAB

I claim:
1. A modified haemoglobin of formuls (HB)-Za in which Za is a residue of an inositol phosphate aldehyde having 2 to 4 phosphate groups.

2. A compound according to claim 1 in polymerized form.

3. A compound according to claim 2, wherein the polymerisation has been effected by glutaraldehyde.

4. A pharmaceutical formulation comprising an oxygen transporting proportion of a compound according to claim 1 in admixture with a pharmaceutically acceptable excipient, diluent or carrier.

5. A pharmaceutical formulation comprising an oxygen transporting proportion of a compound according to claim 2 in admixture with a pharmaceutically acceptable excipient, diluent or carrier.

* * * * *